United States Patent [19]

Torii et al.

[11] Patent Number: 4,656,264

[45] Date of Patent: Apr. 7, 1987

[54] BICYCLIC AZETIDINONE INTERMEDIATES

[75] Inventors: Shigeru Torii, Akaiwa; Hideo Tanaka; Junzo Nogami, both of Okayama; Michio Sasaoka, Itano; Norio Saito, Itano; Takashi Shiroi, Itano, all of Japan

[73] Assignee: Otsuka Kagaku Kabushiki Kaisha, Osaka, Japan

[21] Appl. No.: 869,811

[22] PCT Filed: Sep. 24, 1983

[86] PCT No.: PCT/JP83/00315

§ 371 Date: May 22, 1984

§ 102(e) Date: May 22, 1984

[87] PCT Pub. No.: WO84/01152

PCT Pub. Date: Mar. 29, 1984

Related U.S. Application Data

[63] Continuation of Ser. No. 619,141, May 22, 1984, abandoned.

[30] Foreign Application Priority Data

Sep. 24, 1982 [JP] Japan .................. 57-167051

[51] Int. Cl.[4] .................. C07D 513/04; C07D 501/30; C07D 501/42; C07D 501/52

[52] U.S. Cl. .................................... 540/353; 540/215; 540/229; 540/230

[58] Field of Search ......................................... 540/353

[56] References Cited

PUBLICATIONS

Greene, "Protective Groups in Organic Chem" 1981, pp. 152-192.

McOmie, Protective Groups in Organic Chem. 183 (1973).

*Primary Examiner*—Mark L. Berch
*Attorney, Agent, or Firm*—Armstrong, Nikaido, Marmelstein & Kubovcik

[57] ABSTRACT

An azetidinone compound represented by the formula

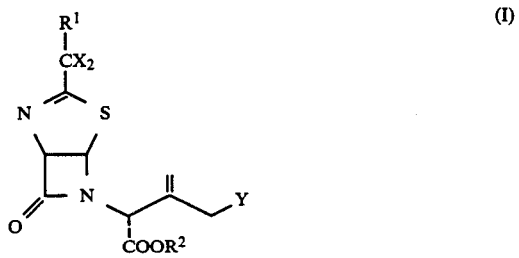

wherein $R^1$ represents a substituted or unsubstituted phenyl group, $R^2$ represents a carboxyl-protecting group, X represents a hydrogen atom or chlorine atom and Y represents —I, —ONO$_2$, —OH,

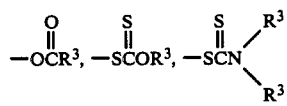

or —SR$^4$ in which R$^3$ is a lower alkyl group or —OR$^5$ (wherein R$^5$ is a halogen-containing lower alkyl group) and R$^4$ is a substituted or unsubstituted, 5-membered aromatic heterocyclic residue containing sulphur and/or nitrogen atom or atoms.

16 Claims, No Drawings

BICYCLIC AZETIDINONE INTERMEDIATES

This application is a continuation of application Ser. No. 619,141 filed May 22, 1984, ABN.

TECHNICAL FIELD AND DISCLOSURE OF THE INVENTION

The present invention relates to novel azetidinone compounds.

The azetidinone compounds of the present invention are novel compounds undisclosed in literature. They are represented by the formula

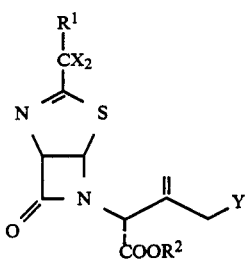

(I)

wherein $R^1$ represents a substituted or unsubstituted phenyl group, $R^2$ represents a carboxyl-protecting group, X represents a hydrogen atom or chlorine atom and Y represents —I, —ONO$_2$, —OH,

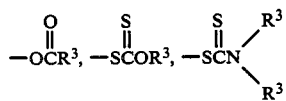

or —SR$^4$ in which R$^3$ is a lower alkyl group or —OR$^5$ (wherein R$^5$ is a halogen-containing lower alkyl group) and R$^4$ is a substituted or unsubstituted, 5-membered aromatic heterocyclic residue containing sulphur and-/or nitrogen atom or atoms.

The azetidinone derivatives of the formula (I) are useful as intermediates for synthesizing cephalosporin-type antibiotics. For example, a cephalosporin compound of the formula (VII) useful as an antibacterial agent can be prepared from the compound of the present invention according to a reaction equation shown below.

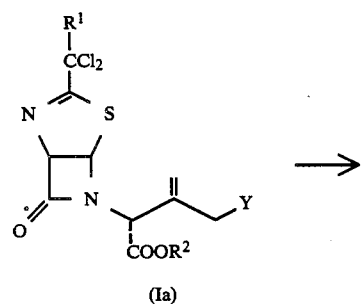

(Ia)

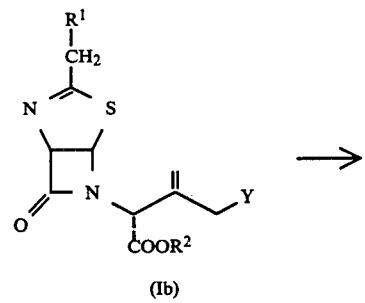

(Ib)

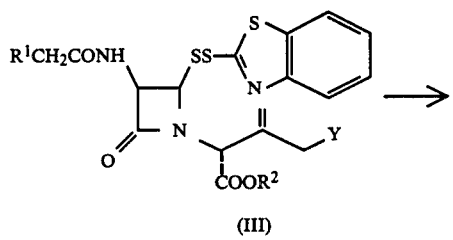

(III)

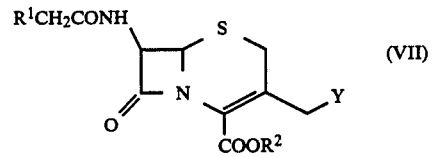

(VII)

In the reaction equation, $R^1$, $R^2$ and Y are as defined above.

Examples of the substituted or unsubstituted phenyl groups represented by $R^1$ in the formula (I) are phenyl, tolyl, xylyl, p-chlorophenyl, p-bromophenyl, p-nitrophenyl, phenyl having protected hydroxyl such as p-methoxyphenyl, etc. Illustrative of carboxyl-protecting groups represented by $R^2$ are methyl, benzyl, diphenyl methyl, p-nitrophenyl, trichloroethyl, etc. Examples of the lower alkyl groups represented by $R^3$ are those having 1 to 4 carbon atoms such as methyl, ethyl, propyl, isopropyl, butyl, etc. Exemplary of the substituted or unsubstituted, 5-membered aromatic heterocyclic residues containing sulphur and/or nitrogen atom or atoms and represented by $R^4$ are 5-methyl-1,3,4-thiadiazole-2-yl, 1-methyl-1,2,3,4-tetrazole-5-yl, 1-phenyl-1,2,3,4-tetrazole-2-yl, 1,3,4-thiadiazole-2-yl, 1,3-thiazole-2-yl, etc. The halogen-containing lower alkyl groups represented by $R^5$ include, for example, 2-chloroethyl, 2-bromoethyl, 2,2-dichloroethyl, 2,2'-dibromoethyl, 2,2,2-trichloroethyl, 2,2,2-tribromoethyl, etc.

The compound (I) of the present invention can be prepared by using a compound of the formula (IV)

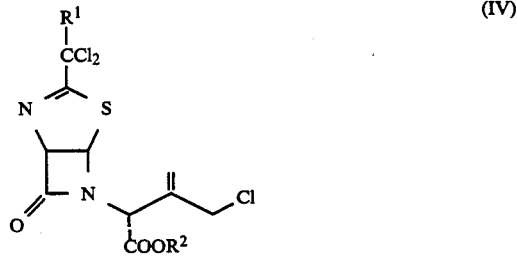

(IV)

wherein R¹ and R² are as defined above as the starting material by various processes as stated hereinafter.

The compound (IV) can be prepared by the conventional method, for example, that reported in Tetrahedron Lett. 22, 3193 (1981).

(1) The compound of the present invention represented by the formula

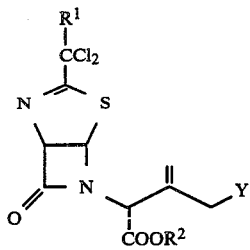

wherein R¹ and R² are as defined above and Y represents —I or

(in which R³ is as defined above) can be prepared by reacting the starting material (IV) with a nucleophilic reagent of the formula

M—Y wherein Y represents —I or

(in which R³ is as defined above) and M represents sodium or potassium atom in an organic solvent. Useful organic solvents can be any of those capable of dissolving the starting compound (IV) and the nucleophilic reagent, such as acetone, methyl ethyl ketone, methyl-isobutyl ketone or like ketones; methyl formate, ethyl formate, methyl acetate, ethyl acetate or like esters; diethyl ether, tetrahydrofuran, dioxane or like ethers; nitromethane, nitroethane or like nitroalkanes; acetonitrile, propionitrile or like nitriles; methanol, ethanol or like alcohols; dimethylformamide, dimethylacetamides or like amides; dimethylsulfoxide; etc. among which acetone and dimethylsulfoxide are preferred. The amount of the organic solvent is not particularly limited but is usually 1 to 200 times, preferably 2 to 50 times, the weight of the compound (IV). The ratio between the compound (IV) and the nucleophilic reagent can be suitably determined over a wide range. Usually about 1 to about 5 moles, preferably about 1 to about 3 moles, of the latter is used per mole of the former. The reaction is carried out at a temperature of usually about −10° to about 70° C., preferably about 10° to about 55° C. and is completed generally in about 0.5 to about 4 hours.

(2) The present compound of the formula

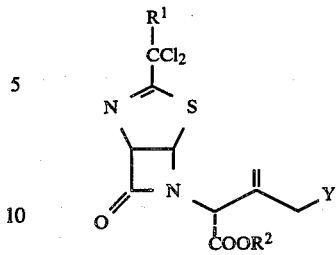

wherein R¹ and R² are as defined above and Y represents

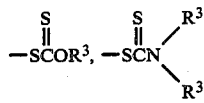

or —SR⁴ (in which R³ and R⁴ are as defined above) can be prepared by reacting the thiazolinoazetidinone compound of the following formula produced by the process described above in (1)

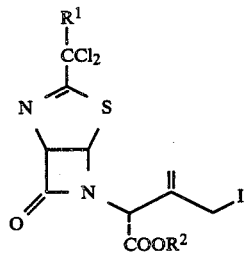 (VI)

wherein R¹ and R² are as defined above with a nucleophilic reagent of the formula

M—Y wherein M represents sodium or potassium atom and Y represents

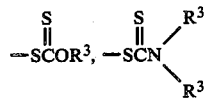

or —SR⁴ (in which R³ and R⁴ are as defined above) in an organic solvent to selectively subject only the iodine atom to nucleophilic substitution. Useful organic solvents can be any of those capable of dissolving the compound (VI) and the nucleophilic reagent. Extensive use is made of the organic solvents to be used in the reaction between the compound (IV) and the nucleophilic reagent. Preferable examples of useful solvents are acetone, dimethylsulfoxide, dimethylformamide or like aprotic solvents among which acetone is more preferable. The amount of the organic solvent is not particularly limited, but is usually 1 to 200 times, preferably 2 to 50 times, the weight of the compound (VI). The ratio between the compound (VI) and the nucleophilic reagent can be suitably determined over a wide range, but the latter is used in an amount of usually 1 to 3 moles, preferably 1 to 1.5 moles, of the former. The reaction is conducted at a temperature of usually about −10° to about 40° C., preferably around room temperature and is completed generally in about 0.1 to about 2 hours.

(3) The compound of the present invention represented by the formula

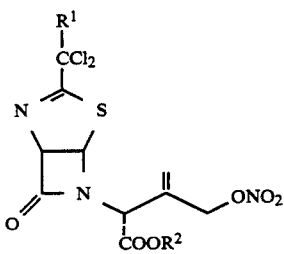

wherein $R^1$ and $R^2$ are as defined above can be prepared by reacting the compound of the following formula (VI) produced by the process stated above in (1):

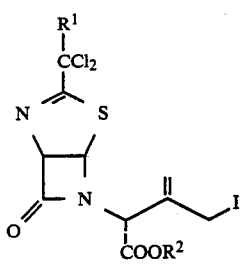
(VI)

wherein $R^1$ and $R^2$ are as defined above with $NaNO_3$ or $KNO_3$ in an organic solvent such as dimethylsulfoxide, dimethylformamide or hexamethylphosphoamide. The organic solvent is used in an amount of usually 1 to 200 times, preferably 2 to 50 times, the weight of the compound (VI). The ratio between the compound (VI) and $NaNO_3$ or $KNO_3$ can be suitably determined over a wide range. Usually about 1 to about 10 moles, preferably about 1 to about 5 moles, of the latter is used per mole of the former. The reaction is effected at a temperature of usually about 0° to about 100° C., preferably about 40° to about 60° C. Preferably the reaction is dine atom with —OH. The amount of the water contained in the solvent is usually about 1 to about 100 moles, preferably about 1 to about 50 moles, per mole of the compound (VI). The solvent is employed in an amount of usually 1 to 200 times, preferably 2 to 50 times, the weight of the compound (VI). Useful acid catalysts include p-toluenesulfonic acid, methanesulfonic acid, trifluoroacetic acid, trichloroacetic acid, dichloroacetic acid and the like. The acid catalyst is used in an amount of usually about 0.1 to about 6 moles, preferably about 0.1 to about 3 moles, per mole of the compound (VI). The reaction is conducted at a temperature of usually 20° to 120° C., preferably 40° to 80° C. and is completed usually in about 1 to about 5 hours.

The compound (wherein $Y = -OH$) thus obtained is reacted with a lower carboxylic acid anhydride or lower carboxylic acid halide having 1 to 5 carbon atoms or a compound represented by the formula

(XI)

wherein $R^5$ represents a halogen-containing lower alkyl group in the presence of pyridine, polyvinyl pyridine, molecular sieve or like acid-trapping agent, thereby giving the compound of the present invention represented by the formula

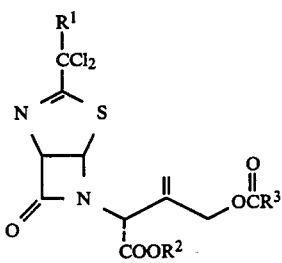

wherein $R^1$, $R^2$ and $R^3$ are as defined above. The reaction is carried out in an organic solvent inert to the reaction. Examples of useful solvents are acetone, metn-

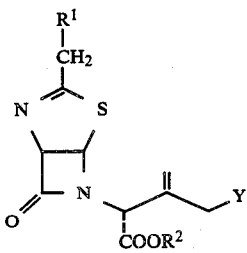

wherein $R^1$ and $R^2$ are as defined above and Y represents —OH,

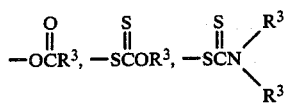

or —$SR^4$ (in which $R^3$ and $R^4$ are as defined above) can be prepared by reacting zinc with the compound of the following formula (Ia) produced by one of the processes stated above in (1) to (3)

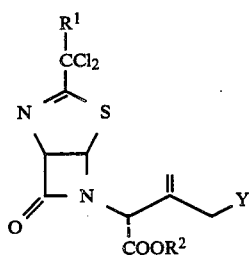

wherein $R^1$ and $R^2$ are as defined above and Y represents —OH,

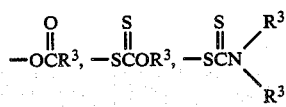

or —$SR^4$ (in which $R^3$ and $R^4$ are as defined above) in an organic solvent in the presence of acetic acid. Useful organic solvents include any of those which is inert to acetic acid and zinc under the following reaction conditions such as acetone, methyl ethyl ketone, methyl-isobutyl ketone and like ketones; diethyl ether, diisopropyl ether, dibutyl ether, tetrahydrofuran, dioxane and like ethers; dichloromethane, dibromomethane, chloroform, bromoform, carbon tetrachloride, dichloroethane, dibromoethane, trichloroethane, and like halogenated hydrocarbons; benzene, toluene, xylene and like aromatic hydrocarbons; methyl formate, ethyl formate, methyl acetate, ethyl acetate, methyl propionate and like esters; acetonitrile, propionitrile and like nitriles; nitromethane, nitroethane, nitropropane and like nitroalkanes; etc. The organic solvent is used in an amount of usually 1 to 200 times, preferably 2 to 50 times, the weight of the compound (Ia). The amount of the acetic acid can be adequately determined over a wide range. The acetic acid is present in the reaction system in an amount of usually about 2 to about 100 moles, preferably about 2 to about 30 moles, per mole of the compound (Ia). The amount of the zinc can also be suitably determined over a wide range. The zinc is used in an amount of usually about 2 to about 10 moles, preferably about 2 to about 4 moles, per mole of the compound (Ia). The reaction is carried out at a temperature of usually −20° to 100° C., preferably −10° to 40° C. and is completed in about 0.5 to about 2 hours.

(5) The compound of the present invention represented by the formula

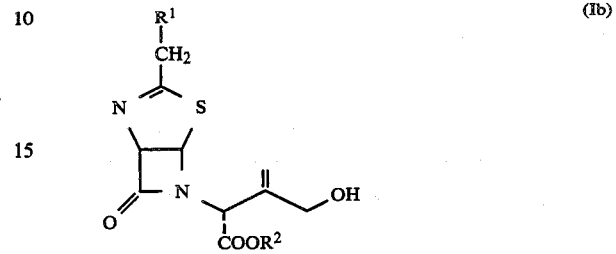

wherein $R^1$ and $R^2$ are as defined above can be prepared by reacting zinc with the compound of the following formula (Ia) produced by the process stated above in (3):

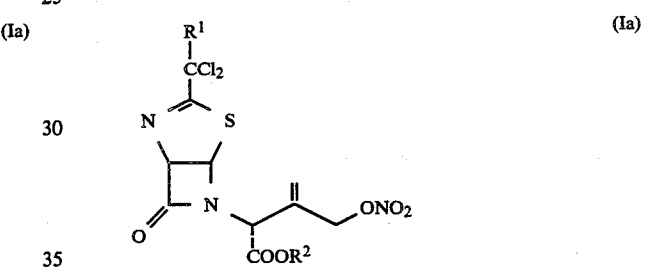

wherein $R^1$ and $R^2$ are as defined above in the presence of acetic acid. The amount of the acetic acid is not particularly limited. The acetic acid is used as a solvent preferably in mixture with another organic solvent. The amount of the zinc can be suitably determined over a wide range, but is usually 5 to 20 moles, preferably 5 to 10 moles, per mole of the compound (Ia). The organic solvent to be used as admixed with the acetic acid can be any of those inert to the reaction, such as ethyl acetate, tetrahydrofuran, methylene chloride, acetone, benzene, etc. The reaction is conducted at usually about −40° to about 80° C., preferably about −20° to about 30° C. and is completed usually in about 0.5 to about 2 hours.

(6) The compound of the present invention represented by the formula

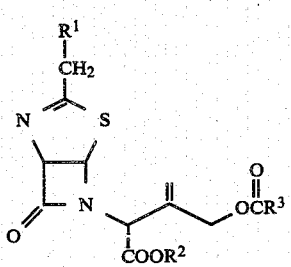

wherein $R^1$, $R^2$ and $R^3$ are as defined above can be prepared by reacting the compound of the following formula produced by the process stated above in (5):

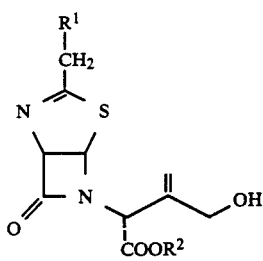

wherein $R^1$ and $R^2$ are as defined above with a lower carboxylic acid anhydride or lower carboxylic acid halide in an organic solvent in the presence of pyridine, polyvinyl pyridine, molecular sieve or like acid-trapping agent. The ratio between the compound (wherein Y=OH) and the lower carboxylic acid anhydride or lower carboxylic acid halide can be appropriately selected from a wide range. Usually the latter is employed in an amount of usually about 1 to about 10 moles, preferably about 1 to about 5 moles, per mole of the former. Useful organic solvents include, for example, acetone, methyl ethyl ketone, methyl-iso-butyl ketone and like ketones; diethyl ether, diisopropyl ether, dibutyl ether, tetrahydrofuran, dioxane and like ethers; dichloromethane, dibromomethane, chloroform, bromoform, carbon tetrachloride, dichloroethane, dibromoethane, trichloroethane and like halogenated hydrocarbons; benzene, toluene, xylene and like aromatic hydrocarbons; methyl formate, ethyl formate, methyl acetate, ethyl acetate, methyl propionate and like esters; acetonitrile, propionitrile and like nitriles; nitromethane, nitroethane, nitropropane and like nitroalkanes; etc. The organic solvent is used in an amount of usually 1 to 200 times, preferably 2 to 50 times, the weight of the starting material. The reaction is effected preferably at a relatively low temperature ranging from about −50° to about 10° C. and is completed generally in about 1 to about 10 hours.

(7) The compound of the present invention represented by the formula

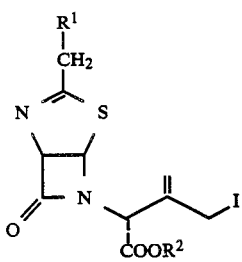

wherein $R^1$ and $R^2$ are as defined above can be prepared by reacting a compound of the following formula produced by the process disclosed in Tetrahedron Letters, 22, 3193 (1981).

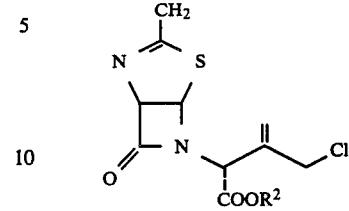

wherein $R^1$ and $R^2$ are as defined above with NaI or KI in the same manner as in the process stated above in (1).

(8) The compound of the present invention represented by the formula

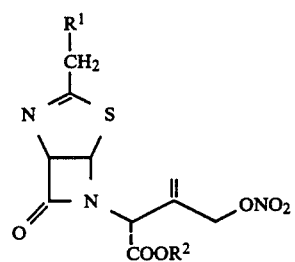

wherein $R^1$ and $R^2$ are as defined above can be prepared by reacting the compound of the following formula produced by the process stated above in (7)

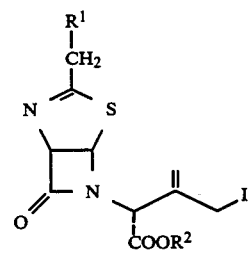

wherein $R^1$ and $R^2$ are as defined above with $NaNO_3$ or $KNO_3$ in the same manner as in the process stated above in (3).

The thiazolinoazetidinone compound of the following formula produced by the foregoing processes

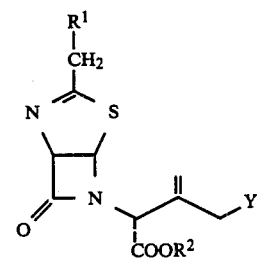

(II)

wherein $R^1$ and $R^2$ are as defined above, Y represents $-ONO_2$,

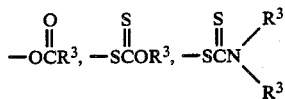

or —SR⁴ in which R³ is lower alkyl or —OR⁵ (wherein R⁵ is a halogen-containing lower alkyl) and R⁴ is a 5-membered aromatic heterocyclic residue containing sulphur and/or nitrogen is reacted with

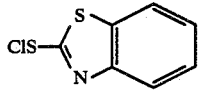

in a hydrous organic solvent to give a compound of the formula

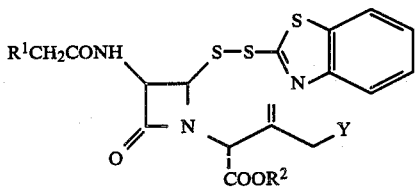

(III)

wherein R¹, R² and Y are as defined above in the formula (II). The water content in the hydrous organic solvent can be properly selected from a wide range but is usually about 1 to about 500 moles, preferably about 10 to about 100 moles, per mole of the compound (II). Exemplary of the organic solvents useful in the reaction are dioxane, tetrahydrofuran, dimethylformamide, dimethylsulfoxide, etc. The hydrous organic solvent is employed in an amount of usually 1 to 200 times, preferably 2 to 50 times, the weight of the compound (II). The ratio between the compound (II) and

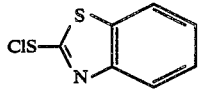

can be suitably determined over a wide range. Usually 1 to 10 moles, preferably 1 to 4 moles, of the latter is used per mole of the former. The reaction is carried out at usually about −10° to about 60° C., preferably around room temperature and is completed generally in about 0.1 to about 1 hour. The compound of the formula

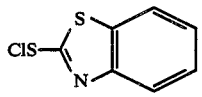

to be used in the rection can be prepared by reacting molecular chloride (Cl₂) with a compound of the formula

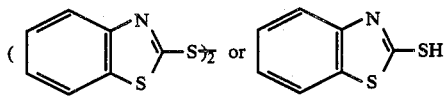

in an inert solvent such as carbon tetrachloride, chloroform, methylene chloride, dioxane, tetrahydrofuran or the like. The compound of the formula

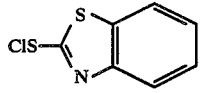

thus obtained may be reacted with the compound (II) as isolated from or as admixed with the reaction mixture. The reaction with the compound (II) in the presence of an inorganic or organic acid may give the product in increased yield. Suitable inorganic acids are sulfuric acid, hydrochloric acid or the like and adequate organic acids are trifluoroacetic acid, p-toluenesulfonic acid or the like. The acid is used in an amount of usually about 0.1 to about 50 moles, preferably about 0.1 to about 10 moles, per mole of the compound (II).

The azetidinone compound of the following formula produced above

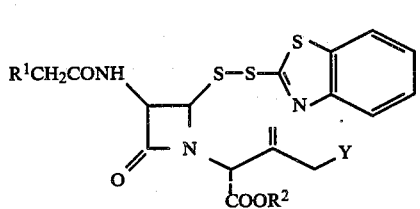

(III)

wherein R¹ and R² are as defined above, Y represents —ONO₂,

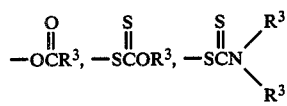

or —SR⁴ in which R³ is a lower alkyl or —OR⁵ (wherein R⁵ is a halogen-containing lower alkyl) and R⁴ is a substituted or unsubstituted, 5-membered aromatic heterocyclic residue containing sulphur and/or nitrogen is reacted with ammonia in a solvent such as dimethylformamide, diethylformamide, diethylacetamide or the like, whereby a cephalosporin compound of the formula

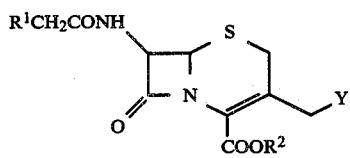

(VII)

wherein R¹, R² and Y are as defined above in the formula (III) can be prepared. The ammonia is used in an amount of usually about 1 to about 10 moles, preferably about 1 to about 3 moles, per mole of the compound (III). The amount of the solvent is usually 1 to 200 times, preferably 2 to 50 times, the weight of the compound (III). The reaction is conducted at usually about −78° to about 20° C., preferably about −40° to about 5° C. and is completed usually in about 0.1 to about 1 hour.

After completion of the reaction, the compounds produced by the processes as detailed above can be extracted and isolated by usual methods and can be purified by column chromatography or recrystallization.

EXAMPLE 1

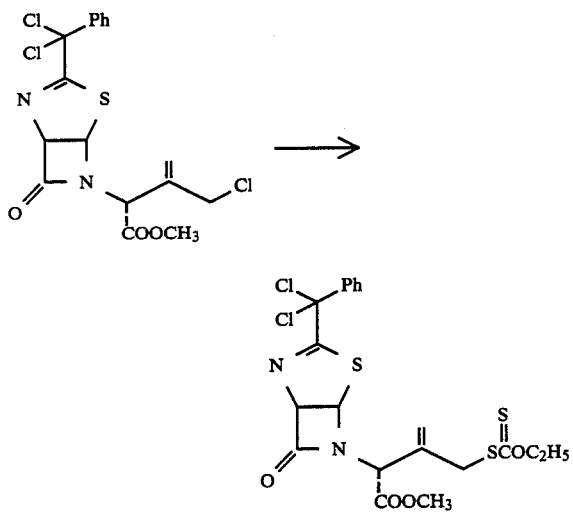

A 4 ml quantity of acetone was added to 249.2 mg of methyl 2-(3-phenyldichloromethyl-7-oxo-4-thia-2,6-diazabicyclo[3,2,0]hepto-2-ene-6-yl)-3-chloromethyl-3-butenate to obtain a uniform solution. To the solution was added 248.5 mg of

and the mixture was subjected to reaction at room temperature for 1 hour. The reaction mixture was diluted with 20 ml of diethyl ether and the dilution was washed with a saturated aqueous solution of sodium chloride and dried over $Na_2SO_4$. The solvent was distilled off at reduced pressure. The resulting pale yellow oily residue was subjected to silica gel column chromatography using benzene-ethyl acetate (10:1), giving 268.5 mg of methyl 2-(3-phenyldichloromethyl-7-oxo-4-thia-2,6-diazabicyclo[3,2,0]hepto-2-ene-6-yl)-3-ethoxythiocarbonylthiomethyl-3-butenate in 90% yield.

NMR (δ, $CDCl_3$) 1.39 (t, 3H, 7 Hz), 3.70 (s, 3H), 4.63 (q, 2H, 7 Hz), 5.04 (s, 1H), 5.11 (s, 1H), 5.39 (s, 1H), 6.02 (s, 2H), 7.20–7.55 (m, 3H), 7.55–7.85 (m, 2H).

EXAMPLE 2

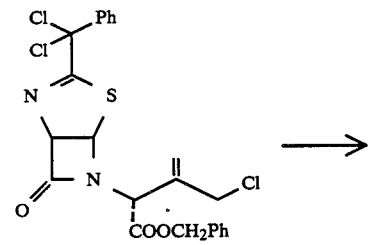

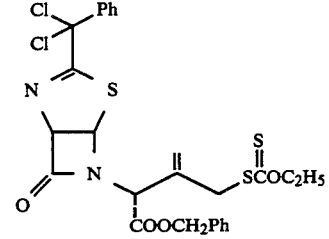

Using as the starting material 50.0 mg of benzyl 2-(3-phenyldichloromethyl-7-oxo-4-thia-2,6-diazabicyclo[3,2,0]hepto-2-ene-6-yl)-3-chloromethyl-3-butenate, the same reaction and treatment as in Example 1 were conducted, giving 49.5 mg of benzyl 2-(3-phenyldichloromethyl-7-oxo-4-thia-2,6-diazabicyclo[3,2,0]hepto-2-ene-6-yl)-3-ethoxythiocarbonylthiomethyl-3-butenate in 85% yield.

IR (neat) 1775, 1735 $cm^{-1}$.

NMR (δ, $CDCl_3$) 1.35 (t, 3H, 7 Hz), 3.70 (s, 2H), 4.59 (q, 2H, 7 Hz), 5.00 (s, 1H), 5.09 (s, 1H), 5.15 (s, 2H), 5.32 (s, 1H), 6.00 (s, 2H), 7.25–7.60 (m, 8H), 7.60–7.85 (m, 2H).

EXAMPLE 3

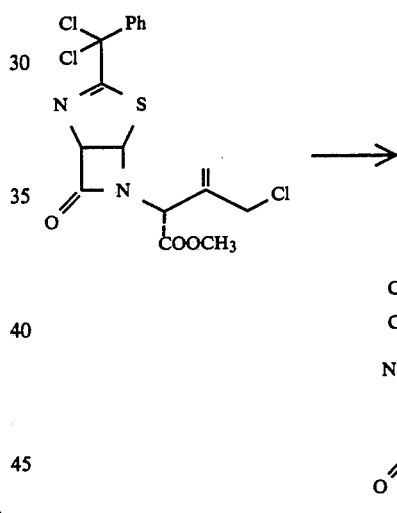

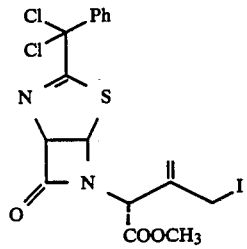

A 1 ml quantity of acetone was added to 30.7 mg of methyl 2-(3-phenyldichloromethyl-7-oxo-4-thia-2,6-diazabicyclo[3,2,0]hepto-2-ene-6-yl)-3-chloromethyl-3-butenate to obtain a uniform solution. To the solution was added 22.0 mg of NaI and the mixture was subjected to reaction for 3 hours while being heated to 55° C. The reaction mixture was cooled to room temperature and was diluted with ethyl acetate. The dilution was washed with an aqueous solution of $Na_2S_2O_3$ and then with a saturated aqueous solution of sodium chloride and dried over $Na_2SO_4$. The solvent was distilled off at reduced pressure. The resulting pale yellow oily residue was subjected to silica gel column chromatography using benzene-ethyl acetate (10:1), giving 30.0 mg of methyl 2-(3-phenyldichloromethyl-7-oxo-4-thia-2,6-diazabicyclo[3,2,0]hepto-2-ene-6-yl)-3-iodomethyl-3-butenate in 81% yield.

IR ($CHCl_3$) 1780, 1745 $cm^{-1}$.

NMR (δ, $CDCl_3$) 3.55 and 3.69 (ABq, 2H, 10 Hz), 3.75 (s, 3H), 5.05 (s, 1H), 5.24 (s, 1H), 5.46 (s, 1H), 6.04 and 6.09 (ABq, 2H, 4 Hz), 7.20–7.60 (m, 3H), 7.60–7.90 (m, 2H).

EXAMPLE 4

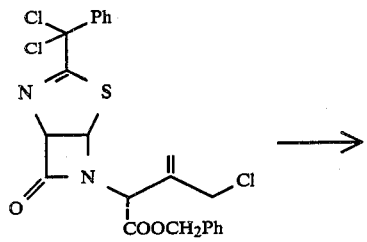

A 5 ml quantity of acetone was added to 450.0 mg of benzyl 2-(3-phenyldichloromethyl-7-oxo-4-thia-2,6-diazabicyclo[3,2,0]hepto-2-ene-6-yl)-3-chloromethyl-3-butenate to obtain a uniform solution. To the solution was added 264.6 mg of NaI and the mixture was heated to 55° C. to continue reaction for 1.5 hours. The reaction mixture was cooled to room temperature and was diluted with ethyl acetate. The dilution was washed with an aqueous solution of $Na_2S_2O_3$ and then with a saturated aqueous solution of sodium chloride and was dried over $Na_2SO_4$. The solvent was removed by distillation at reduced pressure. The resulting pale yellow oily residue was subjected to silica gel column chromatography using benzene-ethyl acetate (80:1), giving 492.0 mg of benzyl 2-(3-phenyldichloromethyl-7-oxo-4-thia-2,6-diazabicyclo[3,2,0]hepto-2-ene-6-yl)-3-iodomethyl-3-butenate in 93% yield.

NMR (δ, $CDCl_3$) 3.53 and 3.67 (ABq, 2H, 10 Hz), 4.94 (s, 1H), 5.18 (s, 2H), 5.30 (s, 1H), 5.39 (s, 1H), 6.03 (s, 2H), 7.33 (s, 5H), 7.15–7.60 (m, 3H), 7.60–7.90 (m, 2H).

EXAMPLE 5

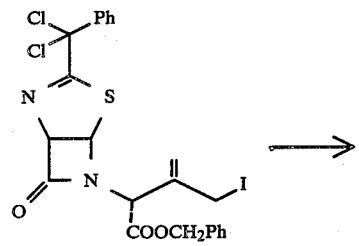

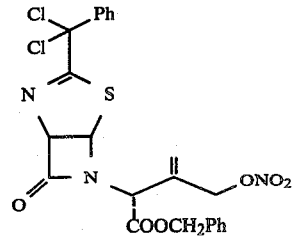

A 0.4 ml quantity of dimethylsulfoxide was added to 25.3 mg of benzyl 2-(3-phenyldichloromethyl-7-oxo-4-thia-2,6-diazabicyclo[3,2,0]hepto-2-ene-6-yl)-3-iodomethyl-3-butenate to obtain a uniform solution. To the solution were added 14.3 mg of $NaNO_3$ and 7.0 mg of methyl methanesulfonate to dissolve therein. The reaction system was heated to 65° C. and subjected to reaction for 2 hours and 40 minutes while being maintained at reduced pressure of 55 mm Hg with use of a water-jet pump. The reaction mixture was left to stand to cool to room temperature and an aqueous solution of $Na_2S_2O_3$ was added, followed by vigorous agitation. The reaction mixture was extracted with ethyl acetate, and the organic layer was washed with a saturated aqueous solution of sodium chloride and was dried over $Na_2SO_4$. The solvent was distilled off at reduced pressure. The resulting yellow oily residue was subjected to silica gel column chromatography using benzene-ethyl acetate (80:1) and then benzene ethyl acetate (10:1), 18.1 mg of benzyl 2-(3-phenyldichloromethyl-7-oxo-4-thia-2,6-diazabicyclo[3,2,0]hepto-2-ene-6-yl)-3-nitroxymethyl-3-butenate in 80% yield.

IR (neat) 1775, 1740, 1635, 1275 $cm^{-1}$.

NMR (δ, $CDCl_3$) 4.74 (s, 2H), 5.04 (s, 1H), 5.18 (s, 2H), 5.23 (s, 1H), 5.44 (s, 1H), 6.02 and 6.06 (ABq, 2H, 4 Hz), 7.32 (s, 5H), 7.15–7.55 (m, 3H), 7.55–7.85 (m, 2H).

EXAMPLE 6-A

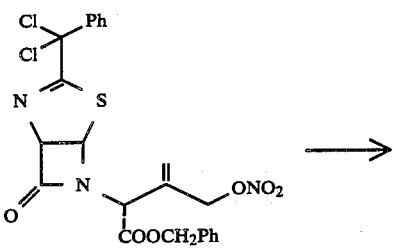

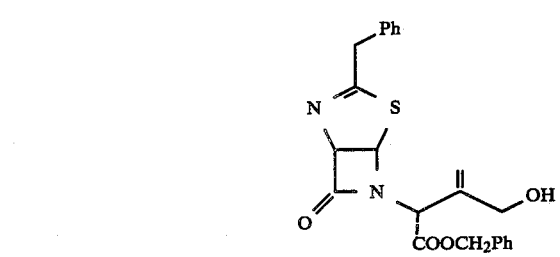

A 0.6 ml quantity of methylene chloride was added to 68.9 mg of benzyl 2-(3-phenyldichloromethyl-7-oxo-4-thia-2,6-diazabicyclo[3,2,0]hepto-2-ene-6-yl)-3-nitroxymethyl-3-butenate to obtain a uniform solution. To the solution was added 42.0 mg of zinc powder and the mixture was cooled to 0° to 5° C., followed by the addition of 0.6 ml of acetic acid. Thereafter the mixture was reacted with stirring for 45 minutes. The reaction mixture was diluted with 5 ml of ethyl acetate and the dilution was washed with a saturated aqueous solution of NaHCO$_3$ and then with a saturated aqueous solution of sodium chloride and dried over Na$_2$SO$_4$. The solvent was distilled off at reduced pressure. The resulting pale yellow oily residue was subjected to silica gel column chromatography using benzene-ethyl acetate (4:1) to provide 46.4 mg of benzyl 2-(3-benzyl-7-oxo-4-thia-2,6-diazabicyclo[3,2,0]hepto-2-ene-6-yl)-3-hydroxymethyl-3-butenate in 85% yield.

IR (neat) 3380, 1770, 1740, 1150 cm$^{-1}$.

NMR (δ, CDCl$_3$) 2.12 (bs, 1H), 3.85 (s, 2H), 3.97 (s, 2H), 5.00 (s, 1H), 5.08 (s, 1H), 5.20 (s, 2H), 5.29 (s, 1H), 5.91 (s, 2H), 7.32 (s, 5H), 7.37 (s, 5H).

EXAMPLE 6-B

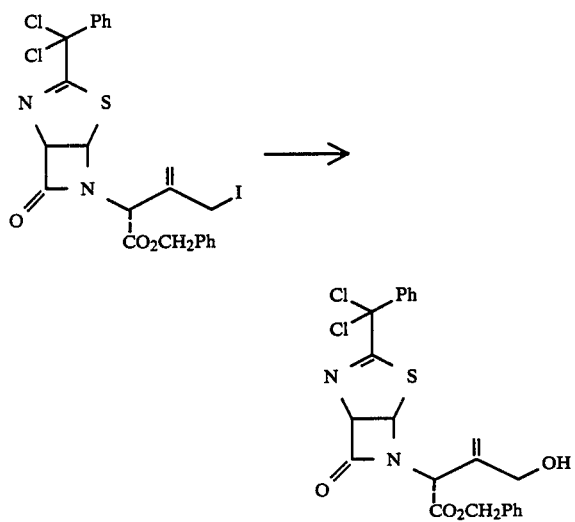

A 0.3 ml quantity of dimethylsulfoxide was added to 35.3 mg of benzyl 2-(3-phenyldichloromethyl-7-oxo-4-thia-2,6-diazabicyclo[3,2,0]hepto-2-ene-6-yl)-3-iodomethyl-3-butenate to give a uniform solution. To the solution was added 14.0 mg of p-toluenesulfonic acid to dissolve therein. The solution was heated to 50° C. to continue reaction for 2 hours. The reaction mixture was allowed to stand to cool to room temperature. An aqueous solution of Na$_2$S$_2$O$_3$ was added thereto and the mixture was vigorously stirred, followed by extraction with ethyl acetate. The organic layer was washed with a saturated aqueous solution of sodium chloride, and was dried over Na$_2$SO$_4$ and the solvent was distilled off at reduced pressure. The resulting yellow oily residue was subjected to silica gel column chromatography using benzene-ethyl acetate (10:1), to afford 22.6 mg of benzyl 2-(3-phenyldichloromethyl-7-oxo-4-thia-2,6-diazabicyclo[3,2,0]hepto-2-ene-6-yl)-3-hydroxymethyl-3-butenate in 78% yield.

IR (neat) 3440, 1780, 1745, 1160 cm$^{-1}$.

NMR (δ, CDCl$_3$) 1.75 (bs, 1H), 4.00 (s, 2H), 5.01 (s, 1H), 5.11 (s, 1H), 5.19 (s, 2H), 5.30 (s, 1H), 6.05 (s, 2H), 7.36 (s, 5H), 7.20–7.60 (m, 3H), 7.60–7.90 (m, 2H).

EXAMPLE 7

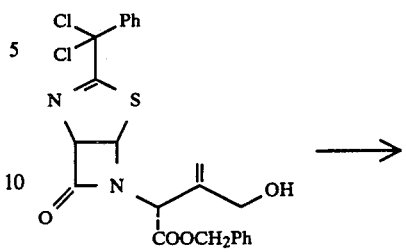

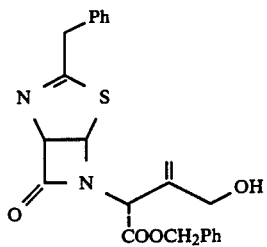

A 22.3 ml quantity of benzyl 2-(3-phenyldichloromethyl-7-oxo-4-thia-2,6-diazabicyclo[3,2,0]hepto-2-ene-6-yl)-3-hydroxymethyl-3-butenate used as the starting material, 6.5 mg of zinc powder and 30 μl of acetic acid were reacted in 0.5 ml of methylene chloride in the same manner as in Example 6, followed by the same treatment as in Example 6, giving 16.8 mg of benzyl 2-(3-benzyl-7-oxo-4-thia-2,6-diazabicyclo[3,2,0]hepto-2-ene-6-yl)-3-hydroxymethyl-3-butenate in 87% yield. The compound thus obtained was chemically analyzed with the same result as that of Example 6.

EXAMPLE 8

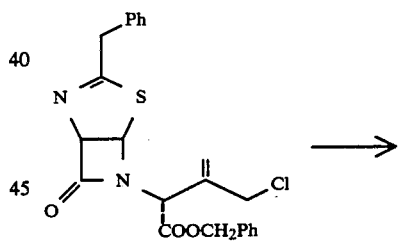

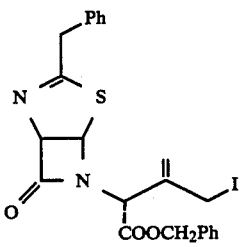

A 1.2 ml quantity of acetone was added to 94.6 mg of benzyl 2-(3-benzyl-7-oxo-4-thia-2,6-diazabicyclo[3,2,0-]hepto-2-ene-3-chloromethyl-3-butenate to obtain a uniform solution. To the solution was added 64.3 mg of NaI and the mixture was agitated for 1.5 hours while being heated to 55° C. The reaction mixture was cooled to room temperature and diluted with 5 ml of ethyl acetate. The dilution was washed with an aqueous solution of Na$_2$S$_2$O$_3$ and then with a saturated aqueous solution of sodium chloride, dried over Na$_2$SO$_4$, and concentrated at reduced pressure, giving 113.0 mg of benzyl 2-(3-benzyl-7-oxo-4-thia-2,6-diazabicyclo[3,2,0-]hepto-2-ene-6-yl)-3-iodomethyl-3-butenate as a colorless oily substance in 99% yield.

NMR (δ, CDCl₃) 3.63 (s, 2H), 3.83 (s, 2H), 4.95 (s, 1H), 5.17 (s, 2H), 5.23 (s, 2H), 5.38 (s, 1H), 5.87 (bs, 2H), 7.26 (s, 5H), 7.33 (s, 5H).

EXAMPLE 9

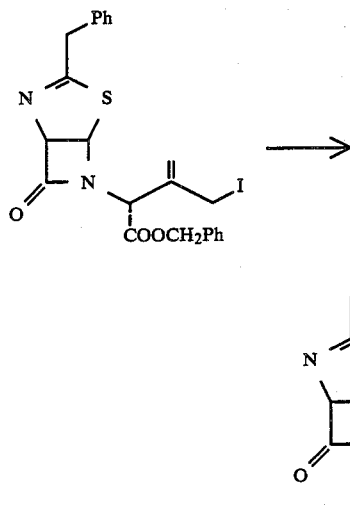

A 0.9 ml quantity of dimethylsulfoxide was added to 103.5 mg of benzyl 2-(3-benzyl-7-oxo-4-thia-2,6-diazabicyclo[3,2,0]hepto-2-ene-6-yl)-3-iodomethyl-3-butenate to obtain a uniform solution. To the solution were added 80 mg of NaNO₃ and 40 mg of methyl methanesulfonate to dissolve therein. The reaction system was heated to 48° C. to react for 4 hours while being maintained at reduced pressure of 45 to 50 mm Hg with use of a water-jet pump. The reaction mixture was left to stand to cool to room temperature and an aqueous solution of Na₂S₂O₃ was added, followed by vigorous stirring. The mixture was extracted with ethyl acetate and the organic layer was washed with a saturated aqueous solution of sodium chloride, dried over Na₂SO₄ and concentrated at reduced pressure. The resulting yellow oily residue was subjected to silica gel column chromatography using benzene-ethyl acetate (15:1) to afford 68.5 mg of benzyl 2-(3-benzyl-7-oxo-4-thia-2,6-diazabicyclo[3,2,0]hepto-2-ene-6-yl)-3-nitroxymethyl-3-butenate in 76% yield.

IR (neat) 1780, 1740, 1640, 1275 cm⁻¹.

NMR (δ, CDCl₃) 3.85 (s, 2H), 4.74 (s, 2H), 5.01 (s, 1H), 5.18 (s, 2H), 5.22 (s, 1H), 5.43 (s, 1H), 5.89 and 5.93 (ABq, 2H, 4 Hz), 7.28 (s, 5H), 7.34 (s, 5H).

EXAMPLE 10

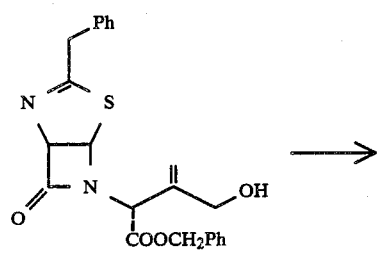

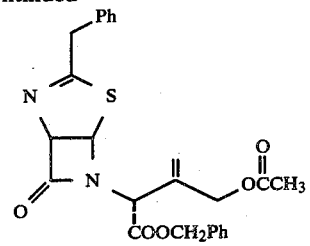

A 0.3 ml quantity of methylene chloride was added to 23.8 mg of benzyl 2-(3-benzyl-7-oxo-4-thio-2,6-diazabicyclo[3,2,0]hepto-2-ene-6-yl)-3-hydroxymethyl-3-butenate to obtain a uniform solution. The solution was cooled to 0° to 5° C. and 22 μl of acetic anhydride and then 12 μl of pyridine were added. The mixture was subjected to reaction for 12 hours. The solvent and the like were distilled off at reduced pressure with use of a vacuum pump. The resulting pale yellow oily residue was subjected to silica gel column chromatography using benzene-ethyl acetate (10:1) to give 24.7 mg of benzyl 2-(3-benzyl-7-oxo-4-thia-2,6-diazabicyclo[3,2,0-]hepto-2-ene-6-yl)-3-acetoxymethyl-3-butenate in 94% yield.

IR (neat) 1775, 1745, 1740 (sh), 1230 cm⁻¹.

NMR (δ, CDCl₃) 2.00 (s, 3H), 3.84 (s, 2H), 4.49 (s, 2H), 5.05 (s, 2H), 5.15 (s, 2H), 5.29 (s, 1H), 5.88 (s, 2H), 7.24 (s, 5H), 7.32 (s, 5H).

EXAMPLE 11

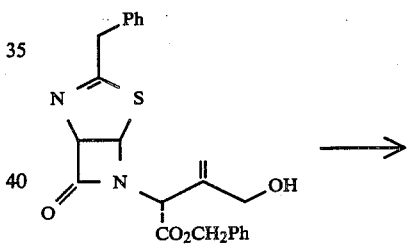

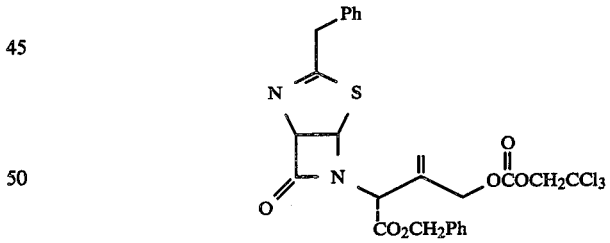

A 0.3 ml quantity of methylene chloride was added to 28.3 mg of benzyl 2-(3-benzyl-7-oxo-4-thia-2,6-diazabicyclo[3,2,0]hepto-2-ene-6-yl)-3-hydroxymethyl-3-butenate to obtain a uniform solution. The solution was cooled to 0° to 5° C., and 14.4 μl of

and then 15.6 μl of pyridine were added to continue reaction for 2.5 hours. To the reaction mixture was added 5% hydrochloric acid and the mixture was extracted with ethyl acetate. The ethyl acetate solution thus obtained was washed with a saturated aqueous solution of sodium chloride and dried over Na$_2$SO$_4$. The solvent was distilled off at reduced pressure. The resulting colorless oily residue was subjected to silica gel column chromatography using benzene-ethyl acetate (20:1) to give 30 mg of benzyl 2-(3-benzyl-7-oxo-4-thia-2,6-diazabicyclo[3,2,0]hepto-2-ene-6-yl)-3-(2,2,2-trichloroethoxycarbonyloxymethyl)-3-butenate in 75% yield.

IR (neat) 1770, 1745 (sh), 1730 (sh), 1235 cm$^{-1}$.

NMR (δ, CDCl$_3$) 3.85 (s, 2H), 4.10 (s, 2H), 4.23 (s, 2H), 5.04 (s, 1H), 5.16 (s, 3H), 5.37 (s, 1H), 5.84 and 5.91 (ABq, 2H, 4 Hz), 7.25 (s, 5H), 7.34 (s, 5H).

EXAMPLE 12

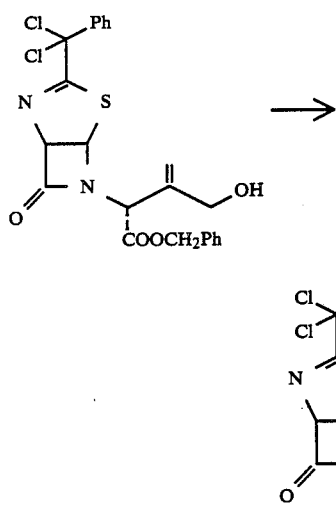

The same procedure as in Example 10 was repeated by using as the starting material 26.0 mg of benzyl 2-(3-phenyldichloromethyl-7-oxo-4-thia-2,6-diazabicyclo[3,2,0]hepto-2-ene-6-yl)-3-hydroxymethyl-3-butenate, producing 27.0 mg of benzyl 2-(3-phenyldichloromethyl-7-oxo-4-thia-2,6-diazabicyclo[3,2,0]hepto-2-ene-6-yl)-3-acetoxymethyl-3-butenate in 96% yield.

IR (neat) 1770, 1740, 1730, 1220 cm$^{-1}$.

NMR (δ, CDCl$_3$) 2.02 (s, 3H), 4.47 (s, 2H), 5.09 (s, 2H), 5.16 (s, 2H), 5.30 (s, 1H), 6.01 (s, 2H), 7.31 (s, 5H), 7.20–7.60 (m, 3H), 7.60–7.90 (m, 2H).

EXAMPLE 13

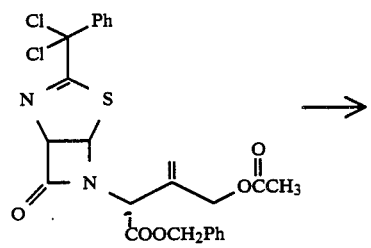

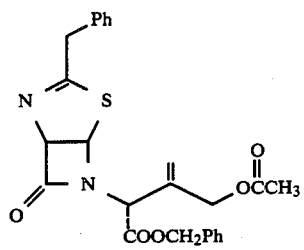

The procedure of Example 7 was followed by using as the starting material 32.0 mg of benzyl 2-(3-phenyldichloromethyl-7-oxo-4-thia-2,6-diazabicyclo[3,2,0]hepto-2-ene-6-yl)-3-acetoxymethyl-3-butenate, producing 25.6 mg of benzyl 2-(3-benzyl-7-oxo-4-thia-2,6-diazabicyclo[3,2,0]hepto-2-ene-6-yl)-3-acetoxymethyl-3-butenate in 92% yield. The product thus obtained was chemically analyzed with the result identical with that of the compound given in Example 10.

EXAMPLE 14

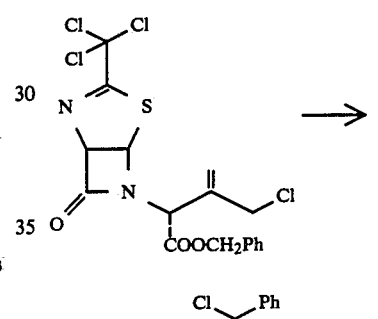

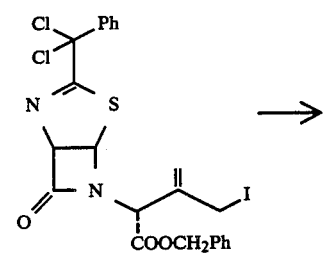

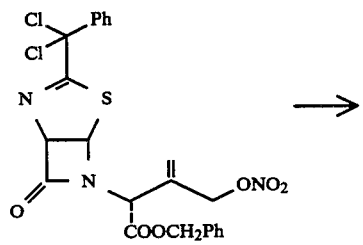

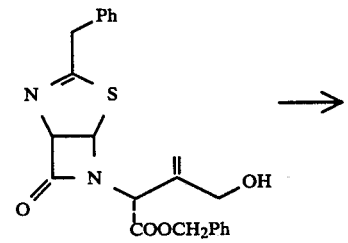

-continued

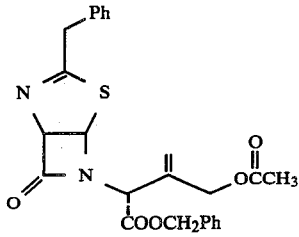

A 2.2 ml quantity of acetone was added to 200.0 mg of benzyl 2-(3-phenyldichloromethyl-7-oxo-4-thia-2,6-diazabicyclo[3,2,0]hepto-2-ene-6-yl)-3-chloromethyl-3-butenate to obtain a uniform solution. To the solution was added 117.6 mg of NaI and the mixture was subjected to reaction for 1.5 hours by being heated to 55° C. The reaction mixture was cooled to room temperature and diluted with ethyl acetate. The dilution was washed successively with an aqueous solution of $Na_2S_2O_3$ and with a saturated aqueous solution of sodium chloride and dried over $Na_2SO_4$. The solvent was distilled off at reduced pressure. To the resulting pale yellow oily residue was added 1.6 ml of dimethylsulfoxide to obtan a uniform solution. To the solution were added 150 mg of $NaNO_3$ and 75.6 mg of methyl methanesulfonate to dissolve therein. The solution was subjected to reaction for 4 hours by being heated to 50° C. while being maintained at reduced pressure of 45 to 52 mm Hg with use of a water-jet pump. The reaction mixture was left to stand to cool to room temperature and an aqueous solution of $Na_2S_2O_3$ was added, followed by vigorous agitation. The resultant mixture was extracted with ethyl acetate and the organic layer was washed with a saturated aqueous solution of sodium chloride and dried over $Na_2SO_4$. The solvent was distilled off at reduced pressure. To the yellow oily residue was added 1.5 ml of methylene chloride to provide a uniform solution. A 128.2 mg quantity of zinc powder was added and the mixture was cooled to 0° to 5° C. To the cooled mixture was added 1.5 ml of acetic acid and the mixture was stirred for 2 hours. The reaction mixture was diluted with ethyl acetate. The dilution was washed with a saturated aqueous solution of $NaHCO_3$ and subsequently with a saturated aqueous solution of sodium chloride and dried over $Na_2SO_4$. The solvent was distilled off at reduced pressure. To the resulting yellow oily residue was added 1.5 ml of methylene chloride to obtain a uniform solution. The solution was cooled to 0° to 5° C., followed by the addition of 0.12 ml of acetic anhydride and of 66 μl of pyridine after which reaction was continued for 16 hours. Subsequently the same procedure as in Example 10 was followed, giving 137 mg of benzyl 2-(3-benzyl-7-oxo-4-thia-2,6-diazabicyclo[3,2,0]hepto-2-ene-6-yl)-3-acetoxymethyl-3-butenate in 75% yield. The product thus obtained was chemically analyzed with the result identical with that of the product obtained in Example 10.

EXAMPLE 15

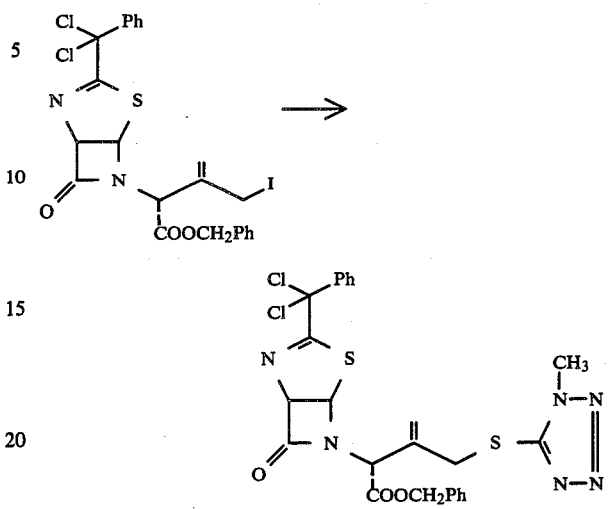

A 0.5 ml quantity of acetone was added to 43.8 mg of benzyl 2-(3-phenyldichloromethyl-7-oxo-4-thia-2,6-diazabicyclo[3,2,0]hepto-2-ene-6-yl)-3-iodomethyl-3-butenate to obtain a uniform solution. To the solution was added 10.5 mg of

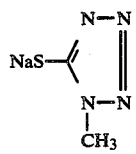

and the mixture was stirred at room temperature for 35 minutes to undergo reaction. The reaction mixture was diluted with 3 ml of ethyl acetate and the dilution was washed successively with an aqueous solution of $Na_2S_2O_3$ and with a saturated aqueous solution of sodium chloride and dried over $Na_2SO_4$. The solvent was distilled off at reduced pressure. The resulting pale yellow oily residue was subjected to silica gel column chromatography using benzene-ethyl acetate (20:1), giving 36.2 mg of benzyl 2-(3-phenyldichloromethyl-7-oxo-4-thia-2,6-diazabicyclo[3,2,0]hepto-2-ene-6-yl)-3-(1-methyl-1,2,3,4-tetrazole-5-yl-thiomethyl)-3-butenate in 89% yield.

IR (neat) 1775, 1740 cm$^{-1}$.

NMR (δ, CDCl$_3$) 3.45 and 3.98 (ABq, 2H, 14 Hz), 3.73 (s, 3H), 4.94 (s, 1H), 5.10 (s, 1H), 5.19 (s, 1H), 5.33 (s, 1H), 6.02 and 6.09 (ABq, 2H, 4 Hz), 7.33 (s, 5H), 7.10–7.60 (m, 3H), 7.60–7.90 (m, 2H).

EXAMPLE 16

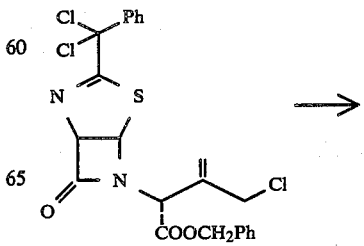

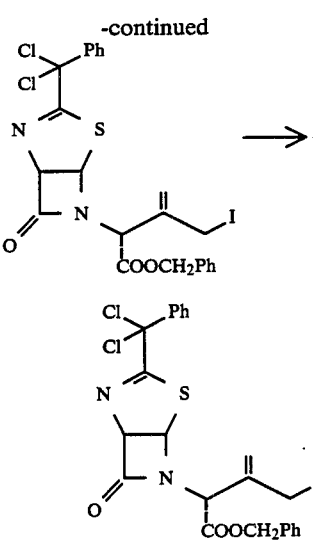

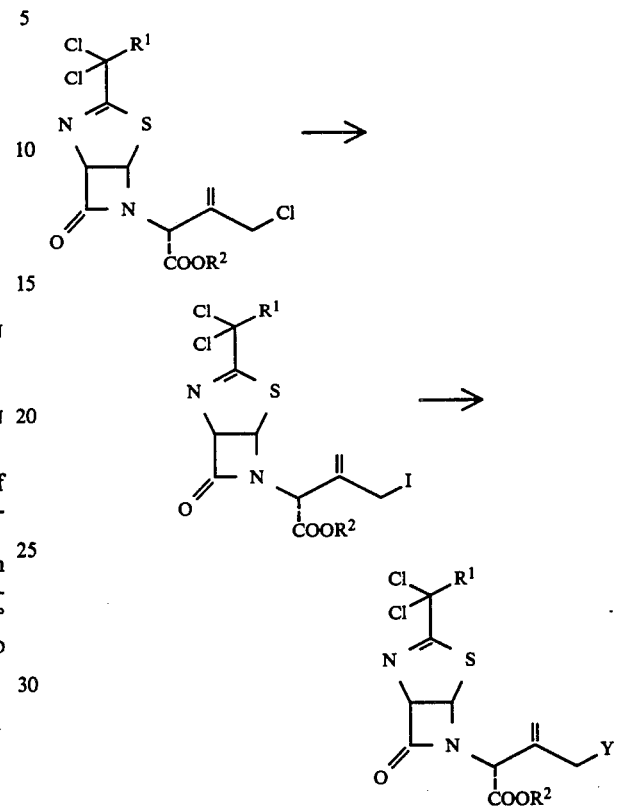

EXAMPLE 17

A 0.5 ml quantity of acetone was added to 37.1 mg of benzyl 2-(3-phenyldichloromethyl-7-oxo-4-thia-2,6-diazabicyclo[3,2,0]hepto-2-ene-6-yl)-3-chloromethyl-3-butenate to obtain a uniform solution. To the solution was added 21.8 mg of NaI and the mixture was subjected to reaction for 2 hours while being heated to 53° C. The reaction mixture was allowed to stand to cool to room temperature and 11.1 mg of

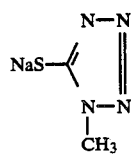

was added. The mixture was stirred at room temperature for 20 minutes to continue reaction. The reaction mixture was treated in the same manner as in Example 14 to give 36.5 mg of benzyl 2-(3-phenyldichloromethyl-7-oxo-4-thia-2,6-diazabicyclo[3,2,0]hepto-2-ene-6-yl)-3-(1-methyl-1,2,3,4-tetrazole-5-yl-thiomethyl)-3-butenate in 85% yield. The compound thus obtained was chemically analyzed with the result identical with that of the compound produced in Example 15.

The compounds as shown below in a table were obtained by following the procedure of Example 16. The table also indicates the yields and the results of chemical analysis.

| $R^1$ | $R^2$ | Y | Yield (%) | IR (cm$^{-1}$) | NMR ($\delta$, CDCl$_3$) |
|---|---|---|---|---|---|
| Ph | PhCH$_2$ | -S-C(=N-N(Ph)-N=N-) (1-phenyltetrazol-5-ylthio) | 95 | 1775, 1740 | 3.55 and 4.08 (ABq, 2H, 14Hz), 5.03 (s, 1H), 5.09 (s, 2H), 5.14 (s, 1H), 5.50 (s, 1H), 5.99 and 6.02 (ABq, 2H, 4Hz), 7.15–7.85 (m, 15H) |
| Ph | PhCH$_2$ | -S-C(=N-N=C(CH$_3$)-S-) (2-methyl-1,3,4-thiadiazol-5-ylthio) | 79 | 1770, 1735 | 2.63 (s, 3H), 3.53 and 3.92 (ABq, 2H, 14Hz), 5.00 (s, 1H), 5.14 (s, 2H), 5.22 (s, 1H), 5.33 (s, 1H), 6.01 and 6.04 (ABq, 2H, 4Hz), 7.20–7.55 (m, 3H), 7.32 (s, 5H), 7.55–7.85 (m, 2H) |
| Ph | PhCH$_2$ | -SC(=S)N(CH$_3$)$_2$ | 90 | 1775, 1745 | 3.33 (bs, 3H), 3.45 (bs, 3H), 4.05 (s, 2H), 5.01 (s, 1H), 5.10 (s, 1H), 5.15 (s, 2H), 5.39 (s, 1H), 5.99 (s, 2H), 7.32 (s, 5H), 7.15–7.55 (m, 3H), 7.55–7.85 (m, 2H) |
| Ph | PhCH$_2$ | -SC(=S)OC$_2$H$_5$ | 75 | 1775, 1735 | The result is identical with that of the compound obtained in Example 2. |

EXAMPLE 18

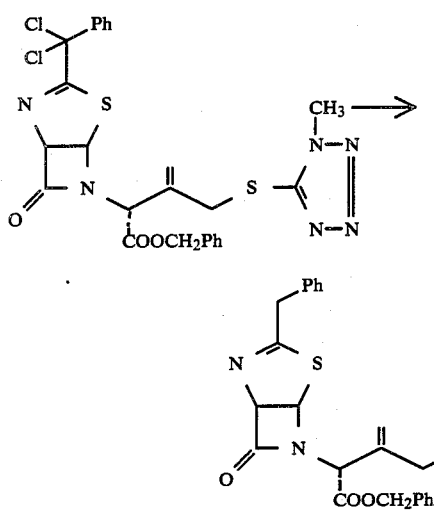

A 0.3 ml quantity of methylene chloride was added to 27.0 mg of benzyl 2-(3-phenyldichloromethyl-7-oxo-4-thia-2,6-diazabicyclo[3,2,0]hepto-2-ene-6-yl)-3-(1-methyl-1,2,3,4-tetrazole-5-yl-thiomethyl)-3-butenate to obtain a uniform solution. To the solution were added 7.5 mg of zinc powder and then 30 μl of acetic acid and the mixture was stirred at room temperature for 10 minutes to undergo reaction. The reaction mixture was diluted with 3 ml of ethyl acetate and the dilution was washed successively with a saturated aqueous solution of NaHCO$_3$ and with a saturated aqueous solution of sodium chloride and dried over Na$_2$SO$_4$. The solvent was distilled off at reduced pressure. The resulting colorless oily residue was subjected to silica gel column chromatography using benzene-ethyl acetate (10:1), giving 20.7 mg of benzyl 2-(3-benzyl-7-oxo-4-thia-2,6-diazabicyclo[3,2,0]hepto-2-ene-6-yl)-3-(1-methyl-1,2,3,4-tetrazole-5-yl-thiomethyl)-3-butenate in 87% yield.

IR (neat) 1770, 1740 cm$^{-1}$.

NMR (δ, CDCl$_3$) 3.47 and 3.93 (ABq, 2H, 14.5 Hz), 3.71 (s, 3H), 3.85 (s, 2H), 4.91 (s, 1H), 5.09 (s, 2H), 5.17 (s, 1H), 5.29 (s, 1H), 5.85 and 5.93 (ABq, 2H, 4 Hz), 7.25 (s, 5H), 7.34 (s, 5H).

EXAMPLE 19

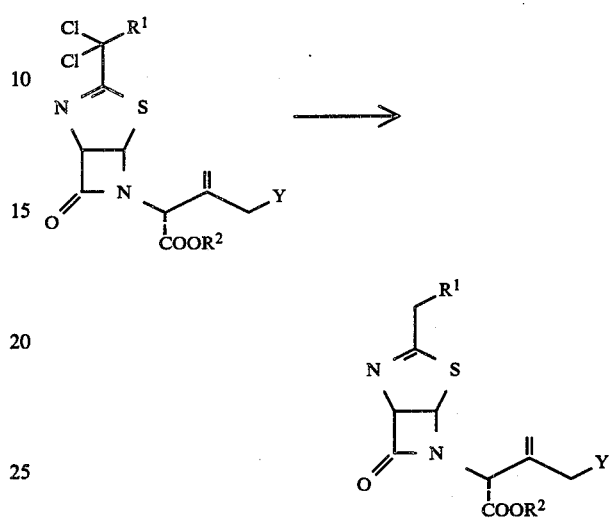

The compounds as shown below in a table were obtained by following the procedure of Example 18. The table also indicates the yields and the results of chemical analysis.

| R$^1$ | R$^2$ | Y | Yield (%) | IR (cm$^{-1}$) | NMR (δ, CDCl$_3$) |
|---|---|---|---|---|---|
| Ph | PhCH$_2$ | -S-C(=N-N(Ph)-N=N-) | 100 | 1775, 1740 | 3.63 and 4.05 (ABq, 2H, 14Hz), 3.80 (s, 2H), 5.02 (s, 1H), 5.08 (s, 2H), 5.12 (s, 1H), 5.48 (s, 1H), 5.86 and 6.01 (ABq, 2H, 4Hz), 7.1–7.6 (m, 15H) |
| Ph | PhCH$_2$ | -S-C(=N-N-)S-C(CH$_3$) | 87 | 1770, 1735 | 3.60 and 3.89 (ABq, 2H, 14.5Hz), 3.83 (s, 2H), 5.00 (s, 1H), 5.14 (s, 2H), 5.20 (s, 1H), 5.35 (s, 1H), 5.85 and 5.92 (ABq, 2H, 4Hz), 7.1–7.5 (m, 10H) |
| Ph | PhCH$_2$ | -SCOC$_2$H$_5$ | 96 | 1770, 1735 | 1.35 (t, 3H, 7Hz), 3.71 (s, 2H), 3.85 (s, 2H), 4.60 (q, 2H, 7Hz), 5.00 (s, 1H), 5.05 (s, 1H), 5.16 (s, 2H), 5.33 (s, 1H), 5.86 and 5.91 (ABq, 2H, 4Hz), 7.25 (s, 5H), 7.31 (s, 5H) |
| Ph | PhCH$_2$ | -SCN(CH$_3$)$_2$ (thiocarbamate) | 79 | 1780, 1745 | 3.35 (bs, 3H), 3.46 (bs, 3H), 3.87 (s, 2H), 4.07 (s, 2H), 5.01 (s, 1H), 5.10 (s, 1H), 5.15 (s, 2H), 5.37 (s, 1H), 5.84 and 5.88 (ABq, 2H, 4Hz), 7.26 (s, 5H), 7.31 (s, 5H) |

REFERENCE EXAMPLE 1

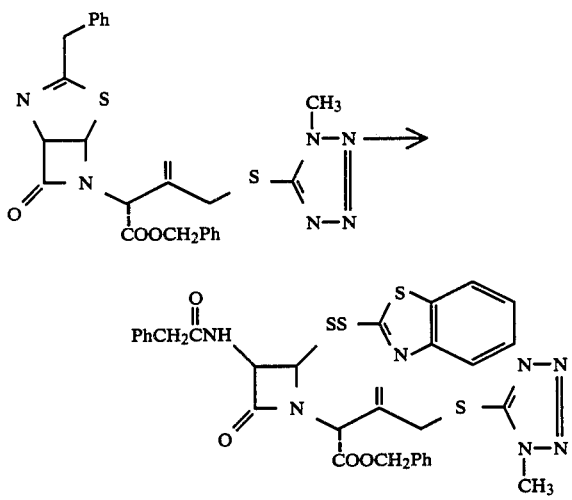

A 0.6 ml quantity of dioxane was added to 29.7 mg of benzyl 2-(3-benzyl-7-oxo-4-thia-2,6-diazabicyclo[3,2,0-]hepto-2-ene-6-yl)-3-(1-methyl-1,2,3,4-tetrazole-5-yl-thiomethyl)-3-butenate to obtain a uniform solution. To the solution was added 60 μl of 5% hydrochloric acid and the mixture was reacted at room temperature for 15 minutes.

Aside from the above procedure, 2 ml of dioxane was added to 37.9 mg of 2-benzothiazolyldisulfide and the mixture was heated in a hot-water bath to obtain a uniform solution. To the solution was added 0.14 ml of a 0.59M solution of chlorine in carbon tetrachloride and the mixture was reacted for 15 minutes. The reaction mixture was added to the dioxane solution obtained above and the mixture was stirred at room temperature to continue reaction for 5 minutes. The reaction mixture was subjected to short silica gel column chromatography using ethyl acetate and the eluate was concentrated at reduced pressure. The resulting residue was dissolved in benzene and the benzene was distilled off at reduced pressure. The residual mixture of colorless solid and colorless oily product thus obtained was subjected to silica gel column chromatography using benzene and then benzene-ethyl acetate (4:1), giving 35.7 mg of benzyl 2-[3-phenylacetamido-4-(2-benzothiazolyldithio)-2-azetidinone-1-yl]-3-(1-methyl-1,2,3,4-tetrazole-5-yl-thiomethyl)-3-butenate in 89% yield.

IR (neat) 3280, 1780, 1740, 1670 cm$^{-1}$.

NMR (δ, CDCl$_3$) 3.69 (s, 2H), 3.74 (s, 3H), 4.19 (s, 2H), 5.10 (s, 3H), 5.23 (dd, 1H, 4.5 Hz, 8 Hz), 5.36 (s, 1H), 5.48 (s, 1H), 5.57 (d, 1H, 4.5 Hz), 6.79 (d, 1H, 8 Hz), 7.1–7.6 (m, 12H), 7.6–8.0 (m, 2H).

REFERENCE EXAMPLE 2

The compounds as shown below in a table were produced by repeating the procedure of Reference Example 1. The table also indicates the yields and the results of chemical analysis.

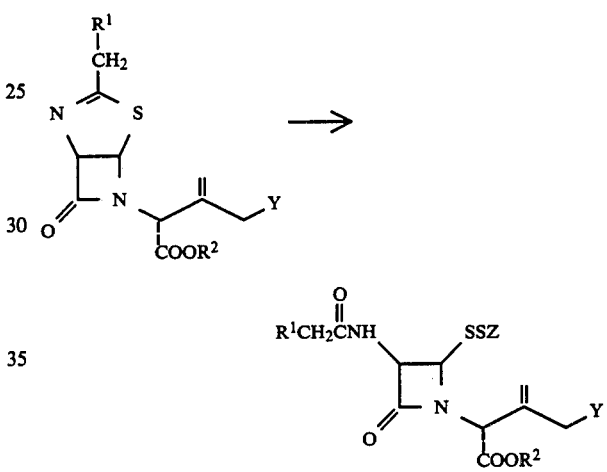

| R$^1$ | R$^2$ | Y | Z | Yield (%) | IR (cm$^{-1}$) | NMR (δ, CDCl$_3$) |
|---|---|---|---|---|---|---|
| PhCH$_2$ | COOCH$_2$Ph | -S-C(=N-N(Ph)-N=N-) | benzothiazolyl | 82 | 3280, 1780, 1740, 1670 | 3.68 (s, 2H), 4.30 (s, 2H), 5.07 (s, 2H), 5.17 (s, 1H), 5.26 (dd, 1H, 4.5Hz, 8Hz), 5.31 (s, 1H), 5.55 (d, 1H, 4.5Hz), 5.59 (s, 1H), 6.83 (d, 1H, 8Hz), 7.1–7.6 (m, 17H), 7.6–8.0 (m, 2H) |
| PhCH$_2$ | COOCH$_2$Ph | -S-C(S-)=N-N=C-CH$_3$ | benzothiazolyl | 72 | 3270, 1780, 1740, 1670 | 2.63 (s, 3H), 3.70 (s, 2H), 4.19 and 4.26 (ABq, 2H, 15Hz), 5.14 (s, 2H), 5.19 (s, 1H), 5.3–5.7 (m, 4H), 7.0–7.6 (m, 13H), 7.6–8.0 (m, 2H) |
| PhCH$_2$ | COOCH$_2$Ph | -SC(=S)OC$_2$H$_5$ | benzothiazolyl | 60 | 3280, 1780, 1740, 1670 | 1.33 (s, 3H, 7Hz), 3.64 (s, 2H), 4.01 (s, 2H), 4.56 (q, 2H, 7Hz), 5.12 (s, 2H), 5.17 (s, 2H), 5.28 (dd, 1H, 4.5Hz, 8Hz), 5.46 (s, 1H), 5.50 (d, 1H, 4.5Hz), 6.76 (d, 1H, 8Hz), 7.1–7.6 (m, 12H), 7.6–8.0 (m, 2H) |

-continued

| R¹ | R² | Y | Z | Yield (%) | IR (cm⁻¹) | NMR (δ, CDCl₃) |
|---|---|---|---|---|---|---|
| PhCH₂ | COOCH₂Ph | $-SC(=S)N(CH_3)_2$ | benzothiazol-2-yl | 45 | 3300, 1780, 1745, 1670 | 3.31 (bs, 3H), 3.39 (bs, 3H), 3.65 (s, 2H), 4.20 and 4.55 (ABq, 2H, 15Hz), 5.13 (s, 3H), 5.25 (s, 1H), 5.29 (dd, 1H, 4.5Hz, 8Hz), 5.50 (s, 1H), 5.52 (d, 1H, 4.5Hz), 6.76 (d, 1H, 8Hz), 7.2–7.6 (m, 12H), 7.6–8.0 (m, 2H) |
| PhCH₂ | COOCH₂Ph | $-ONO_2$ | benzothiazol-2-yl | 70 | 3280, 1780, 1740, 1670, 1640, 1270 | 3.66 (s, 2H), 5.10 (s, 2H), 5.14 (s, 2H), 5.0–5.3 (m, 2H), 5.40 (s, 1H), 5.51 (d, 1H, 5Hz), 5.56 (s, 1H), 6.56 (d, 1H, 7.5Hz), 7.1–7.6 (m, 12H), 7.6–8.0 (m, 2H) |
| PhCH₂ | COOCH₂Ph | $-OC(=O)CH_3$ | benzothiazol-2-yl | 71 | 3280, 1780, 1745, 1670, 1235 | 2.00 (s, 3H), 3.64 (s, 2H), 4.70 (s, 2H), 5.11 (s, 3H), 5.18 (dd, 1H, 5Hz, 8Hz), 5.25 (s, 1H), 5.48 (d, 1H, 5Hz), 6.63 (d, 1H, 8Hz), 7.1–7.6 (m, 12H), 7.6–8.0 (m, 2H), 5.46 (s, 1H) |
| PhCH₂ | COOCH₃ | $-SCOC_2H_5$ | benzothiazol-2-yl | 68 | 3280, 1780, 1735, 1670 | 1.39 (t, 3H, 7Hz), 3.69 (s, 5H), 4.06 (s, 2H), 4.64 (q, 2H, 7Hz), 5.13 (s, 1H), 5.28 (s, 1H), 5.33 (dd, 1H, 4Hz, 8Hz), 5.51 (d, 1H, 4Hz), 5.53 (s, 1H), 6.81 (d, 1H, 8Hz), 7.1–7.6 (m, 7H), 7.6–8.0 (m, 2H) |

REFERENCE EXAMPLE 3

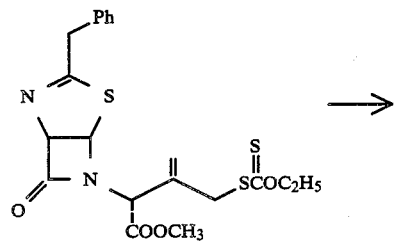

A 0.25 ml quantity of dioxane was added to 25.1 mg of methyl 2-(3-benzyl-7-oxo-4-thia-2,6-diazabicyclo[3,2,0]hepto-2-ene-6-yl)-3-ethoxythiocarbonylthiomethyl-3-butenate to obtain a uniform solution. To the solution was added 50 μl of water.

Aside from the foregoing procedure, 9.4 mg of 2-mercaptobenzothiazole and 14.2 mg of iodine were dissolved in 1 ml of dioxane. The mixture was added to the above dioxane solution and the resulting admixture was reacted at room temperature for 90 minutes. The reaction mixture was diluted with 5 ml of diethyl ether and the dilution was washed successively with an aqueous solution of Na₂S₂O₃ and a saturated aqueous solution of sodium chloride, dried over Na₂SO₄ and concentrated at reduced pressure. The resulting yellow oily residue was subjected to silica gel column chromatography using benzene-ethyl acetate (8:1), giving 23.5 mg of methyl 2-[3-phenylacetamido-4-(2-benzothiazolylthio)-2-azetidinone-1-yl]-3-ethoxythiocarbonylthiomethyl-3-butenate in 67% yield. The compound thus obtained was chemically analyzed with the result identical with that of the compound produced in Reference Example 2.

REFERENCE EXAMPLE 4

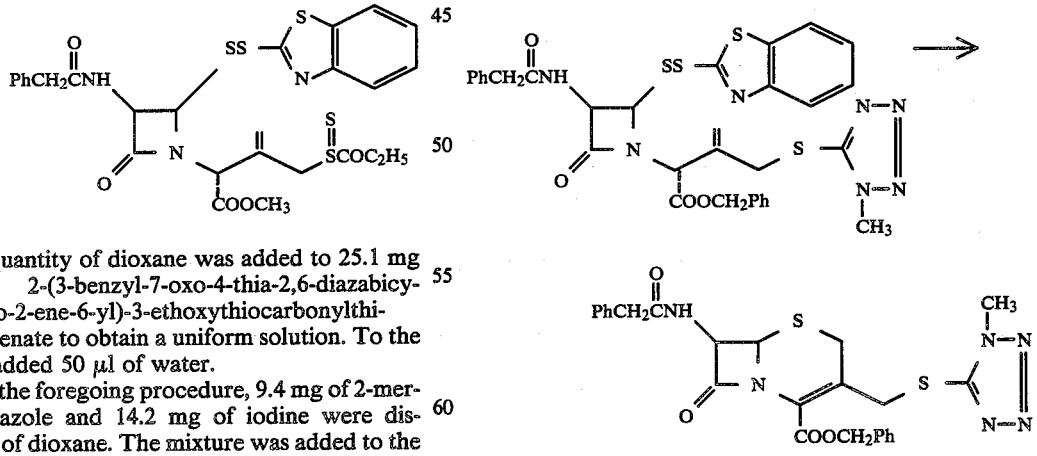

A 0.7 ml quantity of dimethylformamide was added to 35.7 mg of benzyl 2-[3-phenylacetamido-4-(2-benzothiazolyldithio)-2-azetidinone-1-yl]-3-(1-methyl-1,2,3,4-tetrazole-5-yl-thiomethyl)-3-butenate to obtain a uniform solution. The solution was cooled to −30° to −35° C. and thereto was added 23 μl of about 3.3M solution of ammonia gas in dimethylformamide. The mixture was stirred for 15 minutes to undergo reaction. The reaction mixed maintained at −30° C. was subjected to distillation at reduced pressure by a vacuum pump to remove the excess of ammonia, and then was left to stand to cool to room temperature while the solvent was distilled off. The resulting pale yellow oily residue was subjected to silica gel column chromatography using benzene and then benzene-ethyl acetate (4:1), giving 24.6 mg of benzyl 7-phenylacetamido-3-(1-methyl-1,2,3,4-tetrazole-5-yl-thiomethyl)-3-cephem-4-carboxylate in 90% yield.

NMR (δ, CDCl$_3$) 3.61 (s, 2H), 3.66 (s, 2H), 3.84 (s, 3H), 4.25 and 4.45 (ABq, 2H, 13 Hz), 4.90 (d, 1H, 5 Hz), 5.27 (s, 2H), 5.79 (dd, 1H, 5 Hz, 7.5 Hz), 6.35 (d, 1H, 7.5 Hz), 7.30 (s, 5H), 7.47 (s, 5H).

REFERENCE EXAMPLE 5

The compounds as shown below in a table were produced by repeating the procedure of Reference Example 4. The table also indicates the yields and the results of chemical analysis.

| R$^1$ | R$^2$ | Y | Z | Yield (%) | NMR (δ, CDCl$_3$) |
|---|---|---|---|---|---|
| PhCH$_2$ | COOCH$_2$Ph | −S−C(=N−N(Ph)−N=N−) (1-phenyl-tetrazol-5-yl-thio) | benzothiazol-2-yl | 89 | 3.60 (s, 2H), 3.65 (s, 2H), 4.23 and 4.61 (ABq, 2H, 14Hz), 4.86 (d, 1H, 5Hz), 5.26 (s, 2H), 5.75 (dd, 1H, 5Hz, 7.5Hz), 6.50 (d, 1H, 7.5Hz), 7.25 (s, 5H), 7.33 (s, 5H), 7.50 (s, 5H) |
| PhCH$_2$ | COOCH$_2$Ph | −S−C(=N−N−C(CH$_3$)=S−) (5-methyl-1,3,4-thiadiazol-2-yl-thio) | benzothiazol-2-yl | 86 | 2.68 (s, 3H), 3.62 (s, 4H), 4.14 and 4.64 (ABq, 2H, 14Hz), 4.90 (d, 1H, 5Hz), 5.30 (s, 2H), 5.80 (dd, 1H, 5Hz, 9Hz), 6.45 (d, 1H, 9Hz), 7.30 (s, 5H), 7.36 (s, 5H) |
| PhCH$_2$ | COOCH$_2$Ph | −SCOC$_2$H$_5$ (C=S) | benzothiazol-2-yl | 82 | 1.40 (t, 3H, 7Hz), 3.44 and 3.53 (ABq, 2H, 18Hz), 3.61 (s, 2H), 4.16 and 4.48 (ABq, 2H, 14Hz), 4.64 (q, 2H, 7Hz), 4.89 (d, 1H, 4.5Hz), 5.26 (s, 2H), 5.78 (dd, 1H, 4.5Hz, 8.5Hz), 6.37 (d, 1H, 8.5Hz), 7.30 (s, 5H), 7.36 (s, 5H) |
| PhCH$_2$ | COOCH$_2$Ph | −SCN(CH$_3$)$_2$ (C=S) | benzothiazol-2-yl | 85 | 3.35 (bs, 3H), 3.56 (bs, 5H), 3.61 (s, 2H), 4.37 and 4.75 (ABq, 2H, 14Hz), 4.90 (d, 1H, 5Hz), 5.25 (s, 1H), 5.77 (dd, 1H, 5Hz, 9Hz), 6.18 (d, 1H, 9Hz), 7.30 (s, 5H), 7.37 (s, 5H) |
| PhCH$_2$ | COOCH$_2$Ph | −ONO$_2$ | benzothiazol-2-yl | 73 | 3.36 and 3.48 (ABq, 2H, 18Hz), 3.60 (s, 2H), 4.93 (d, 2H, 5Hz), 5.16 and 5.58 (ABq, 2H, 12Hz), 5.25 (s, 2H), 5.83 (dd, 1H, 5Hz, 8Hz), 6.33 (d, 1H, 8Hz), 7.28 (s, 5H), 7.34 (s, 5H) |
| PhCH$_2$ | COOCH$_2$Ph | −OCCH$_3$ (C=O) | benzothiazol-2-yl | 84 | 2.01 (s, 3H), 3.35 and 3.46 (ABq, 2H, 18Hz), 3.60 (s, 2H), 4.82 and 5.03 (ABq, 2H, 13Hz), 4.93 (d, 1H, 4Hz), 5.24 (s, 2H), 5.82 (dd, 1H, 4Hz, 9Hz), 6.53 (d, 1H, 9Hz), 7.30 (s, 5H), 7.37 (s, 5H) |
| PhCH$_2$ | COOCH$_2$Ph | −S-benzothiazol-2-yl | benzothiazol-2-yl | 92 | 3.67 (bs, 2H), 4.19 and 4.89 (ABq, 2H, 14Hz), 4.55 (s, 2H), 4.94 (d, 1H, 5Hz), 5.36 (s, 2H), 5.88 (dd, 1H, 5Hz, 10Hz), 6.7–8.1 (m, 15H) |

| R[1] | R[2] | Y | Z | Yield (%) | NMR (δ, CDCl₃) |
|---|---|---|---|---|---|
| PhCH₂ | COOCH₂Ph | (N-methyl tetrazolylthio group) | tetrachlorophenyl | 75 | 3.61 (s, 2H), 3.66 (s, 2H), 3.84 (s, 3H), 4.25 and 4.45 (ABq, 2H, 13Hz), 4.90 (d, 1H, 5Hz), 5.27 (s, 2H), 5.79 (dd, 1H, 5Hz, 7.5Hz), 6.35 (d, 1H, 7.5Hz), 7.30 (s, 5H), 7.47 (s, 5H) |

We claim:

1. An azetidinone compound of the formula

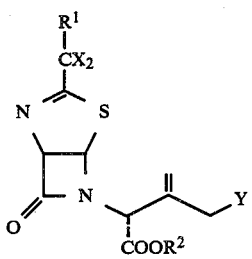

wherein:
R[1] is selected from the group consisting of phenyl, tolyl, xylyl, p-chlorophenyl, p-bromophenyl, p-nitrophenyl and p-methoxyphenyl,
R[2] is a carboxyl-protecting group,
X is hydrogen or chlorine, and
Y is —ONO₂.

2. An azetidinone compound as defined in claim 1 wherein R[1] is phenyl.

3. An azetidinone compound as defined in claim 1 wherein R[2] is methyl, benzyl, diphenylmethyl, p-nitrophenyl or trichloroethyl.

4. An azetidinone compound of the formula

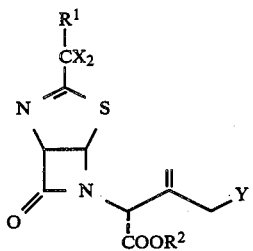

wherein:
R[1] is selected from the group consisting of phenyl, tolyl, xylyl, p-chlorophenyl, p-bromophenyl, p-nitrophenyl and p-methoxyphenyl,
R[2] is a carboxyl-protecting group,
X is hydrogen or chlorine, and
Y is

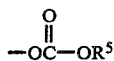

wherein R[5] is a halogen-substituted lower alkyl group.

5. An azetidinone compound as defined in claim 4 wherein R[1] is phenyl.

6. An azetidinone compound as defined in claim 4 wherein R[2] is methyl, benzyl, diphenylmethyl, p-nitrophenyl or trichloroethyl.

7. An azetidinone compound of the formula

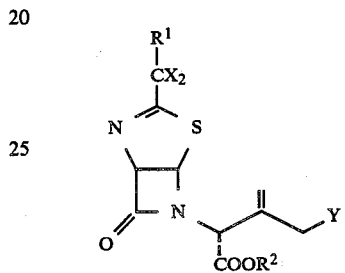

wherein:
R[1] is selected from the group consisting of phenyl, tolyl, xylyl, p-chlorophenyl, p-bromophenyl, p-nitrophenyl and p-methoxyphenyl,
R[2] is a carboxyl-protecting group,
X is hydrogen or chlorine, and
Y is

wherein R[3] is a lower alkyl.

8. An azetidinone compound as defined in claim 7 wherein R[1] is phenyl.

9. An azetidinone compound as defined in claim 7 wherein R[2] is methyl, benzyl, diphenylmethyl, p-nitrophenyl or trichloroethyl.

10. An azetidinone compound of the formula

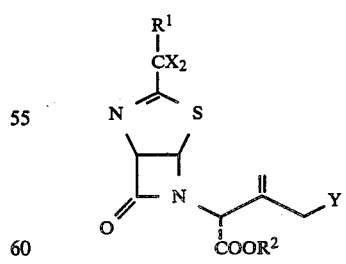

wherein:
R[1] is selected from the group consisting of phenyl, tolyl, xylyl, p-chlorophenyl, p-bromophenyl, p-nitrophenyl and p-methoxyphenyl,
R[2] is a carboxyl-protecting group,
X is hydrogen or chlorine, and
Y is

wherein $R^3$ is a lower alkyl.

11. An azetidinone compound as defined in claim 10 wherein $R^1$ is phenyl.

12. An azetidinone compound as defined in claim 10 wherein $R^2$ is methyl, benzyl, diphenylmethyl, p-nitrophenyl or trichloroethyl.

13. An azetidinone compound of the formula

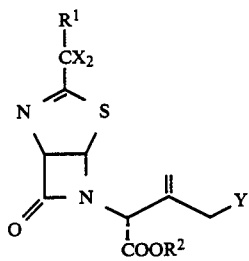

wherein:
$R^1$ is selected from the group consisting of phenyl, tolyl, xylyl, p-chlorophenyl, p-bromophenyl, p-nitrophenyl and p-methoxyphenyl,
$R^2$ is a carboxyl-protecting group,
X is hydrogen or chlorine, and
Y is $-SR^4$ wherein $R^4$ is a 5-member aromatic heterocyclic residue containing at least one heteroatom selected from the group consisting of sulfur and nitrogen, said 5-member aromatic heterocyclic residue optionally having at least one substituent selected from the group consisting of methyl and phenyl.

14. An azetidinone compound as defined in claim 13 wherein $R^1$ is phenyl.

15. An azetidinone compound as defined in claim 13 wherein $R^2$ is methyl, benzyl, diphenylmethyl, p-nitrophenyl or trichloroethyl.

16. An azetidinone compound as defined in claim 13 wherein Y is $-SR^4$ wherein $R^4$ is 5-methyl-1,3,4-thiadiazole-2-yl, 1-methyl-1,2,3,4-tetrazole-5-yl, 1-phenyl-1,2,3,4,-tetrazole-2-yl, 1,3,4-thiadiazole-2-yl or 1,3-thiazole-2-yl.

* * * * *